United States Patent [19]

Norem et al.

[11] Patent Number: 4,813,267

[45] Date of Patent: Mar. 21, 1989

[54] THERMAL CONDUCTIVITY DETECTOR

[75] Inventors: Stanley D. Norem, Bayside, N.Y.;
Henry W. Bullinger, Wilton, Conn.

[73] Assignee: The Perkin-Elmer Corporation, Norwalk, Conn.

[21] Appl. No.: 22,147

[22] Filed: Mar. 5, 1987

[51] Int. Cl.[4] ........................................... G01N 31/08
[52] U.S. Cl. ................................... 73/23.1; 73/27 R
[58] Field of Search ............... 73/23.1, 27 R; 422/89; 436/161

[56] References Cited

U.S. PATENT DOCUMENTS

| | | | |
|---|---|---|---|
| 2,585,959 | 2/1952 | Minter | 73/27 R |
| 2,687,036 | 8/1954 | Minter | 73/27 R |
| 3,097,520 | 7/1963 | Thompson | 73/27 R |
| 3,481,179 | 12/1969 | Howarth | 73/27 R |
| 3,603,134 | 3/1970 | Norem | 73/27 R |
| 3,607,084 | 9/1971 | Mackey | 73/27 R |
| 3,687,631 | 8/1972 | Zegel | 73/27 R |
| 3,791,195 | 2/1974 | Loe | 73/27 R |

FOREIGN PATENT DOCUMENTS

| | | | |
|---|---|---|---|
| 465367 | 8/1925 | Fed. Rep. of Germany | 73/27 R |
| 2091882 | 8/1982 | United Kingdom | 73/27 R |

Primary Examiner—Stewart J. Levy
Assistant Examiner—Hezron E. Williams
Attorney, Agent, or Firm—Francis L. Masselle; Edwin T. Grimes; Ronald G. Cummings

[57] ABSTRACT

A thermal conductivity cell is described whose elements are well protected against short term temperature fluctuations, changes in flow rates, leaks, and vapor pressures of construction materials. The sample and reference chambers are formed within a relatively large copper block with a controlled thermal time constant. The thermal elements are isolated from the gas flow paths by porous metal plugs which are thermally "clamped" to the block. Element feed-throughs are potted in thermally conductive epoxy to minimize the effect of temperature gradients.

10 Claims, 5 Drawing Sheets

THERMAL CONDUCTIVITY DETECTOR

TECHNICAL FIELD

The field of this invention is that of detectors for use in analytical chemical instruments and more particularly, detectors for use in gas chromatographs; carbon, hydrogen, nitrogen (CHN) elemental analyzers, and the like.

BACKGROUND ART

U.S. Pat. No. 3,603,134 issued Sept. 7, 1971 to one of the present inventors and is assigned to the same assignee. That patent discloses and claims a detector having a cell comprising a metal block defining sample and reference chambers for receiving the effluent and carrier gases, respectively, of a chromatographic column. Hot wire detectors are mounted in the gas flow stream passing through each chamber. The cell is surrounded by carrier gas for reducing gas leakage between surrounding atmosphere and the detector chambers. The detector contemplated by the present invention also finds application in CHN analyzers such as that disclosed in U.S. Pat. No. 3,698,869.

DISCLOSURE OF INVENTION

The present invention is an improvement of that disclosed in the above-referenced patent. Specifically, the sensing and reference elements are given improved protection against short term fluctuations in the surrounding temperature, against flow rate changes in the sample and reference gases, and against leaks. Also, construction materials having significant vapor pressures are avoided. These changes permit the employment of carrier gases such as argon whose thermal conductivity is only slightly different from that of the sample gases. The resulting signals are relatively weak and are electronically amplified.

Specifically, the sensing elements are symmetrically disposed in a metal block of high thermal conductivity. The block is suspended in a housing, the space between being purged with an inert gas such as the carrier. Sintered plugs in the sample and reference flow paths within the block isolate the element from the gas flow path, but do not prevent their rapid response to changes in the gas components. A deliberate heat leak is provided to control the thermal time constant of the cell. Electrical feedthroughs are potted in thermally conductive resin, further to immunize the detector against temperature gradients.

BEST MODE FOR CARRYING OUT THE INVENTION

Figure 1:
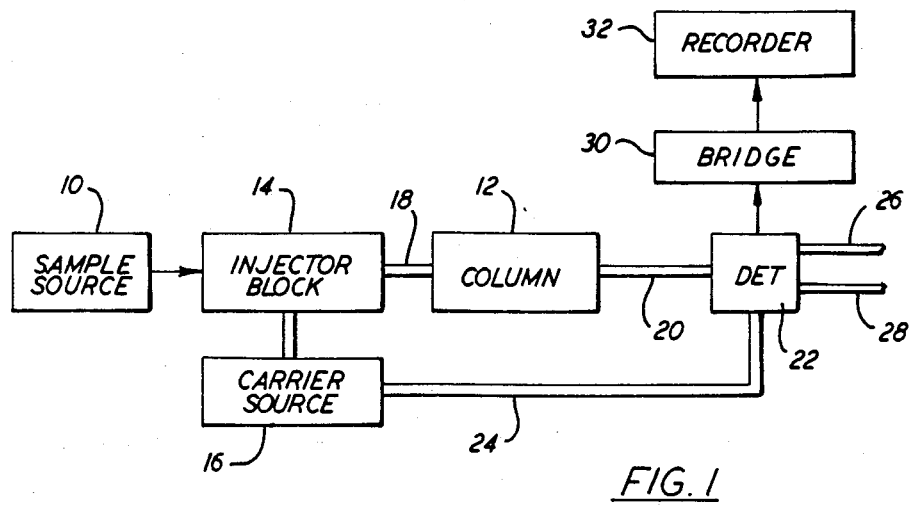
FIG. 1 is a diagram in block form of a gas chromatograph embodying the present invention.

With particular reference to FIG. 1 there is illustrated a gas chromatograph employing the detector of this invention. A sample to be analyzed is derived from the sample source 10 and introduced into the chromatographic column 12 through an injector block 14. Carrier gas, such as argon or helium, is supplied from a source 16 to the injector block 14. The sample, which is vaporized by insertion into the heated injector block, is carried by the carrier gas through a tube 18 to the column 12. In well-known fashion, the column 12 causes the constituents of the sample to separate and successively elute from the column.

The separated constituents are carried by the carrier gas through tube 20 to a detector 22. Detector 22 includes electrical sensing elements responsive, respectively, to the sample/carrier from column 12 and to a reference gas. The carrier gas may function as the reference gas for the detector and is introduced to the detector through tube 24. A vent 26 exhausts the carrier gas and sample to atmosphere, and a vent 28 similarly exhausts the reference gas. The sensing elements in the detector 22 are connected in a bridge circuit 30 whose amplified output is supplied to a recorder 32.

Figure 3:
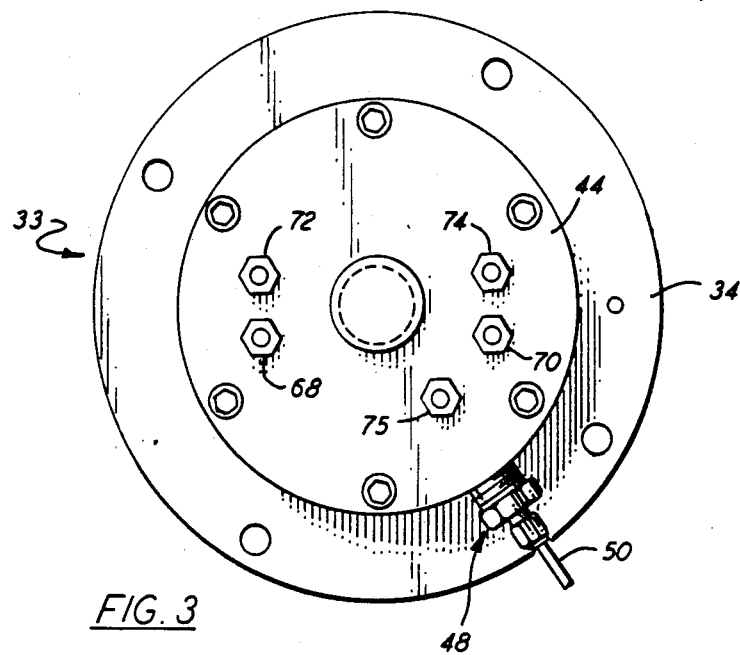
FIG. 3 is a top view of the detector of FIG. 2.
Figure 2:
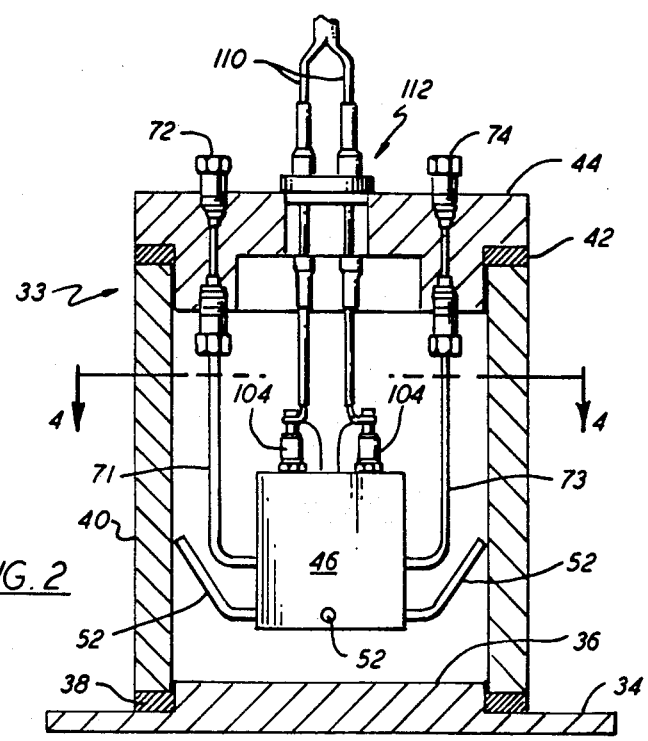
FIG. 2 is an elevational cross-section of a detector in accordance with the present invention.

In order to insure that the detector indications are an accurate representation of the relative concentrations of the sample constituents, the sensing elements should be isolated from influences which could otherwise interfere with accurate indications. FIGS. 2 and 3 illustrate a detector in accordance with the present invention which achieves this objective. It comprises a housing 33 which includes a circular base 34 having a central boss 36. Surrounding the boss 36 is an annular gasket 38. Positioned atop the gasket 38 is a cylindrical aluminum cylinder 40. Mounted atop the cylinder 40 is a second annular gasket 42 which provides a seal for a cover 44. Together the base 34, cylinder 40, and cover 44 form a housing for a cell 46 mounted therein. A fitting 48 through the wall of cylinder 40 connects to a tube 50 for injecting an inert gas, which may be the carrier, into the interior of the housing 33.

Figure 5:
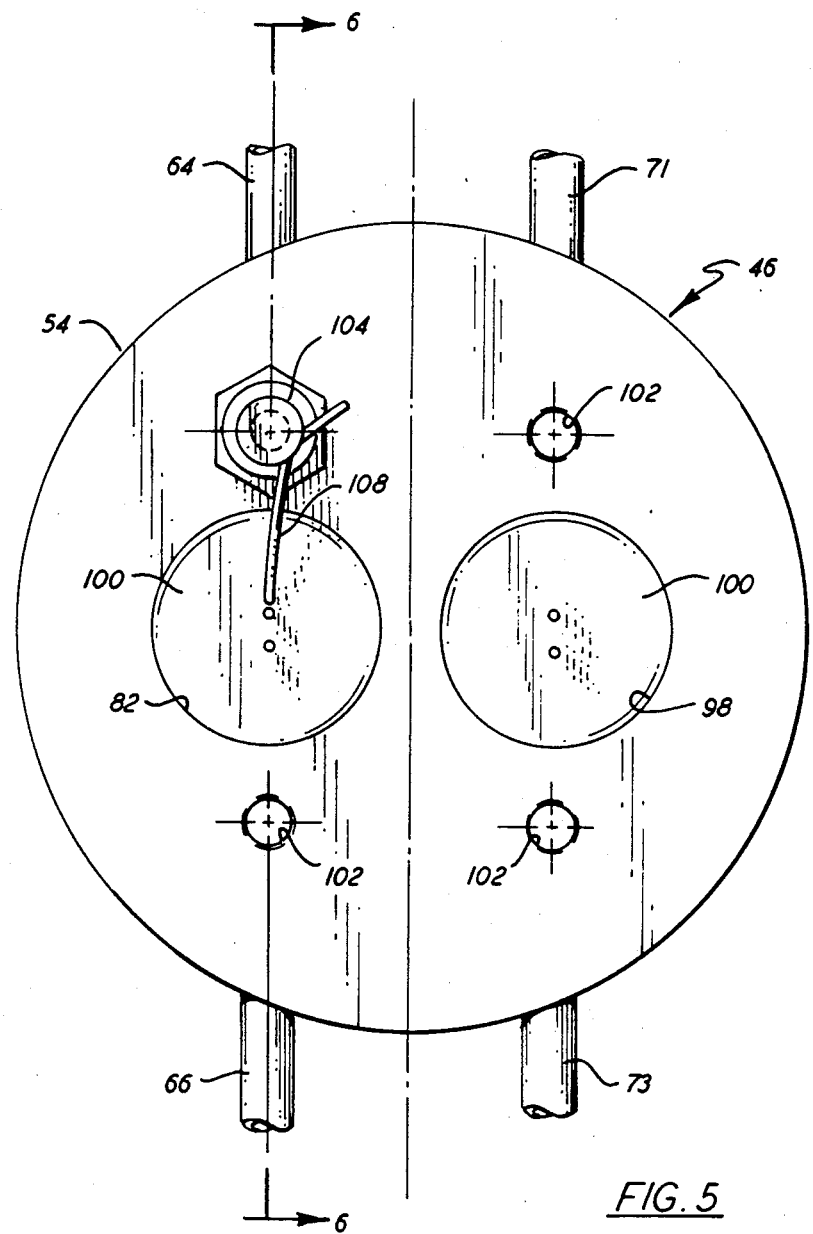
FIG. 5 is an enlarged top view of the cell portion of the structure embodying the invention.

The cell 46 is a cylindrical solid block 54 of copper which is positioned within the housing by four copper wires 52. These wires create a deliberate heat leak which controls the thermal time constant of the cell 46. The construction of cell 46 will be best appreciated from the following description taken in connection with FIGS. 5 and 6.

Figure 6:
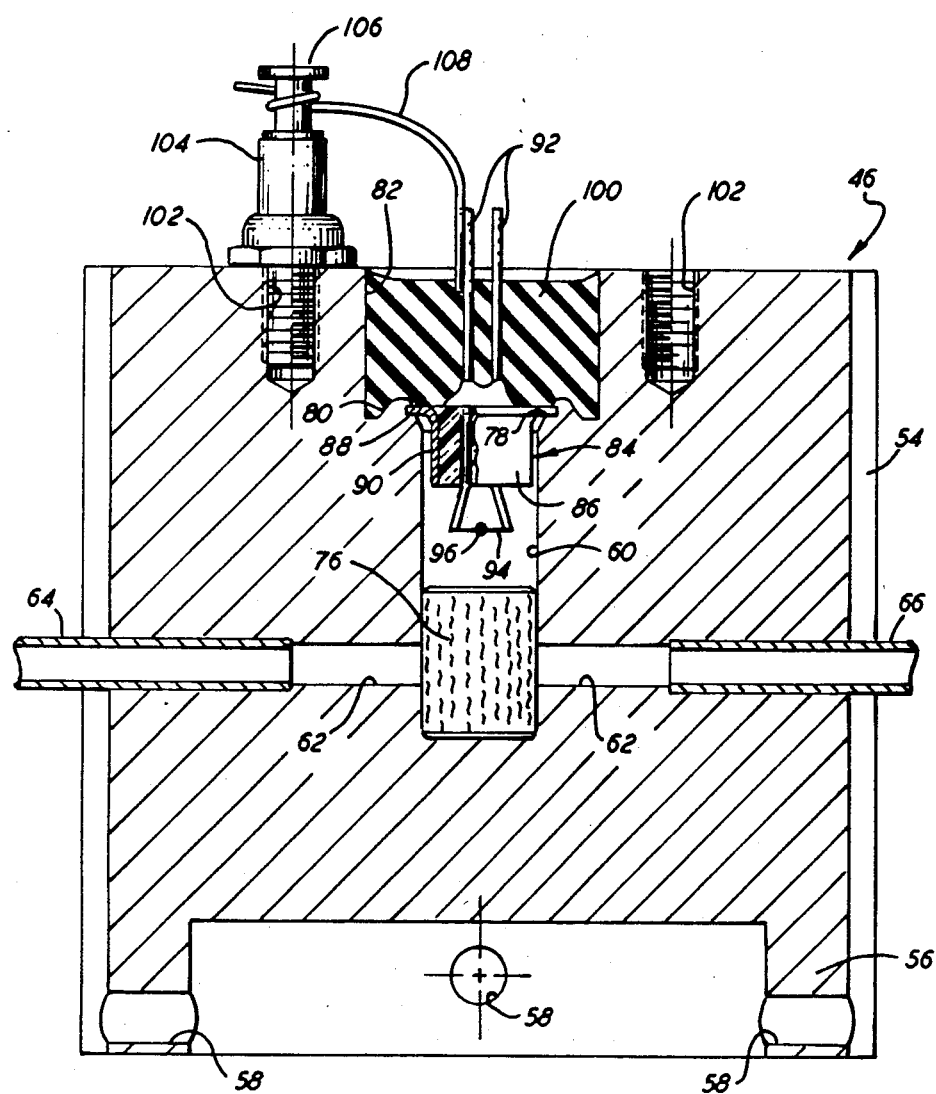
FIG. 6 is a cross-section taken substantially along the line 6—6 of FIG. 5.

A skirt 56 around the bottom edge of the block 54 defines openings 58 which may be used to support the inner ends of heat leak wires 52, previously described. The block 54 defines a pair of symmetrically located cylindrical chambers, a sample chamber 60 as shown in FIG. 6 and a reference chamber which is identical and is accordingly not illustrated. As will be seen in FIG. 6, a sample gas passage 62 passes through the chamber 60 and is connected to a sample inlet tube 64 and a sample outlet tube 66. By means of standard fittings well known to those skilled in the art, the sample inlet tube 64 is connected through the cover 44 of the housing to a sample inlet fitting 68 (FIG. 3) which would normally connect to the tube 20 shown in FIG. 1. Similarly the sample outlet tube 66 is connected through the cover 44 to a sample vent fitting 70. The reference chamber connects in a similar fashion through inlet tube 71 to reference input fitting 72 and through outlet tube 73 to reference vent fitting 74 (FIG. 3). In addition to the sample and reference inlets and vents, the cover 44 of the housing 33 also carries a vent fitting 75 to the interior of the housing.

At the bottom of the sample chamber 60 is a plug 76 of sintered silver. This plug is directly in the path of gases passing through passage 62. The plug 76 may typically be 50% porous and have a pore size equal to, or greater than, 20 microns. It is press-fitted, and thereby thermally clamped, into the copper block 54.

Figure 7:
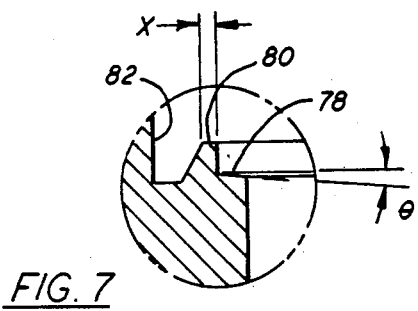
FIG. 7 is an enlarged detail of one feature of the invention.

As will be noted from FIG. 6 the upper end of the chamber 60 is widened to create an annular seat 78. As best appears in the detail of FIG. 7 where shown prior to welding. The seat is surrounded by a tapered ring 80 of copper. A cylindrical well 82 extends from the upper surface of the block 54 and surrounds the tapered ring 80.

Figure 4:
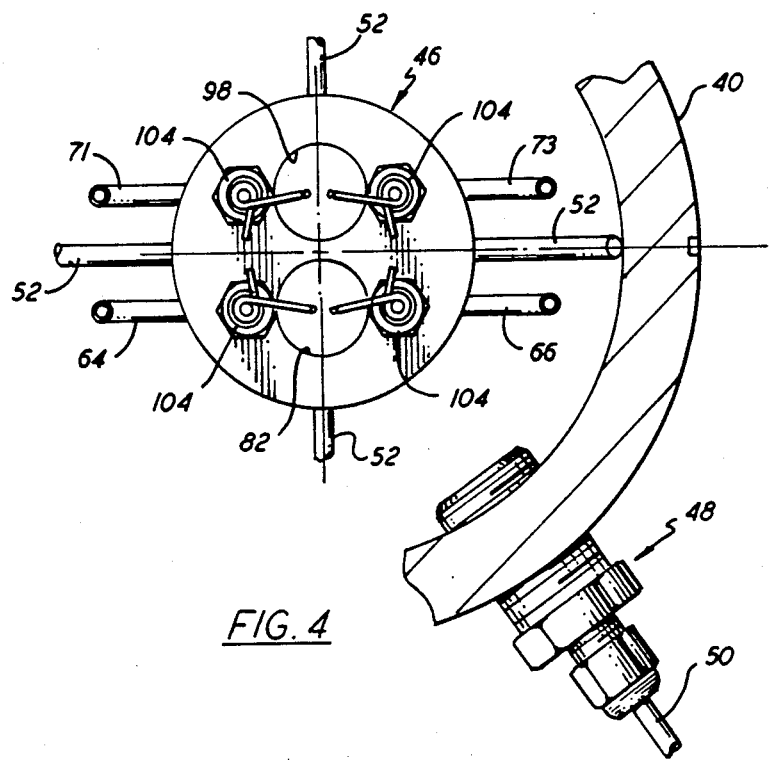
FIG. 4 is a partial cross-section taken substantially along the line 4—4 of FIG. 2.

Mounted within the upper end of the chamber 60 is a thermistor assembly 84 (FIG. 6). The thermistor assembly 84 comprises a generally cylindrical eyelet 86 having a flange 88 which rests upon the seat 78 surrounding the upper end of the chamber 60. The eyelet 86 is of fold-flashed KOVAR (a Westinghouse trademark). Secured within the eyelet 86 by means of a glass fill 90 are a pair of gold-flashed KOVAR leads 92. The leads 92 extend from above the upper surface of block 54 to below the lower surface of eyelet 86 where they are spread as shown in FIG. 6. Supported between their lower ends is a platinum alloy lead 94 which supports a thermistor bead 96. A corresponding reference chamber well (FIG. 4) is similarly configured.

It will be understood that the reference chamber contains a thermistor assembly substantially identical to thermistor assembly 84. These assemblies must be hermetically sealed within their respective chambers. However, it is desirable to avoid the use of materials such as elastomers or cements which possess even slight vapor pressure or might deteriorate with time. Electron beam welding in vacuo produces a clean permanent seal between the copper block 54 and the flange 88 of the thermistor bead assembly 84. The seat design illustrated in detail in FIG. 7 permits rapid local heating and fusion of the copper at the seal without undue heating of the entire block and thermistor (whose temperature should not exceed 300° C.).

The upper surface of the block 54 is drilled and tapped to provide four threaded holes 102. Threaded into these holds are four standoffs 104. (See FIGS. 4, 5 and 6) These provide terminals 106 (one shown, FIG. 6) which are connected to the thermistor leads 92 by means of copper wire 108. Electrical conductors 110 (FIG. 2) bring the thermistor outputs through the cover 44 of the aluminum housing via a header assembly 112.

The apparatus described above has a number of significant features which should be noted. For example, the thermistor elements are symmetrically disposed in a copper block 54 which is suspended in an enclosing chamber formed by the housing 33. The space between the housing and the block is purged with carrier gas which is admitted through the connector 48 and exits through the vent 75. As previously explained, the sintered plugs 76 are thermally clamped to the copper block 54. Accordingly, each presents a surface to its thermistor chamber whose temperature is constant and substantially unaffected by the rate of flow of gas through the detector. Their porosity is such that diffusion is not seriously inhibited and the composition of the gas surrounding the thermistor bead is rapidly represen-
tative of that in the flow stream. In a CHN analyzer, the flow might typically decay from 0.7 cc per second to 0.6 cc per second over the course of one analytical cycle. It is desirable that the base line require no correction for flow sensitivity and that signals be due only to change in gas composition. These objectives have been achieved in this exemplary instrument.

A deliberate heat leak may be provided, especially in the case of argon, by the use of the wires 52 to control the thermal time constant of the cell. Electron beam welding and fluxless vacuum brazing are employed in joining operations. Feedthroughs for the thermistor elements are potted in thermally conductive epoxy.

The entire detector assembly rests in a thermostatically controlled, high velocity air bath which is not a feature of this invention. The average temperature of the bath is precisely controlled. The turbulence and line voltage perturbations may cause rapid small fluctuations which are effectively filtered by the assembly.

EXAMPLE

In one specific example of a detector constructed in accordance with this invention, the copper block 54 had a diameter of 1" and a length of 1". The sample and reference chambers were each approximately 0.157" in diameter. The thermistor assemblies were as described above. They were matched as to resistance, voltage, and current. Each of the porous sintered silver plugs 76 had a length of 0.19" and a diameter of 0.160".

The diameter of the eyelet 86 of thermistor assembly 84 was 0.130". The angle $\Theta$ of seat 78 was 4°, which matched the similar angle of the bottom of the flange 88 of the thermistor assembly 84. The thickness x (see FIG. 7) of the ring 80 was 0.015–0.020". The well 82 and the corresponding well 98 for the reference chamber were filled with an epoxy casting resin 100 such as CASTALL 301 which has a relatively high thermal conductivity.

Figure 8:
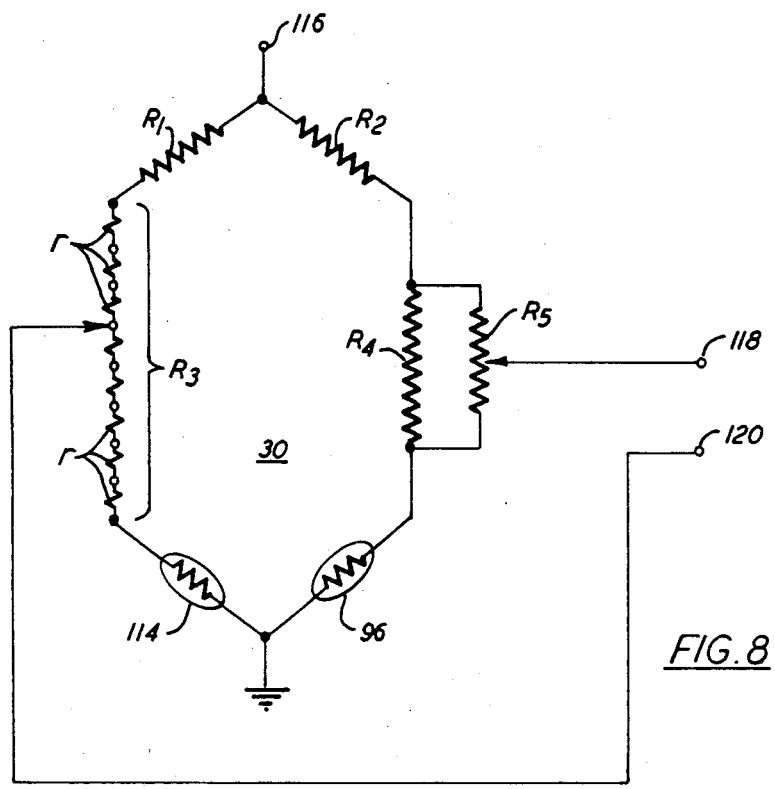
FIG. 8 is a schematic diagram of a bridge circuit usable with the present invention.

Illustrated in FIG. 8 is a bridge circuit including sensing thermistor 96 and reference thermistor 114. In a typical application the values of the resistances of bridge 30 might be as follows:

$R_1 = 3600 \, \Omega$
$R_2 = 3600 \, \Omega$
$r = 10 \, \Omega$
$R_3 = 80 \, \Omega$
$R_4 = 80 \, \Omega$
$R_5 = 1000 \, \Omega$ Input terminal 116 might be connected to 19 volts for a helium carrier and 12 volts for an argon carrier. Output terminals 118, 120 are connected to a recorder amplifier.

When a helium carrier is employed, the presence of sample gases will cause the temperature of sensing thermistor 96 to rise. Its resistance falls and the output at terminal 120 becomes larger than that at 118. When an argon carrier is employed, the presence of sample gases will cause the temperature of sensing thermistor 96 to fall. Its resistance rises and the output of terminal 118 becomes greater than that of terminal 120.

When helium is employed as a carrier gas, the cell is effectively coupled thermally to the case by gaseous conduction. The rise in temperature of the cell due to power dissipated in the thermistors is negligible. When argon is used as a carrier, it has been found advantageous to employ the heat leaks previously described. These are the copper wires 52 between the cell and the inner wall of the housing. They permit reasonably rapid equilibration on start up and negligible temperature self-rise. The heat capacity of the cell is about 10 calorie/k and the thermal resistance of four 2 centimeter lengths of 0.063" diameter copper wire in parallel is about 25 cgs units. This gives an RC thermal time constant of approximately four minutes which is a good compromise between effective filtering and rapid equilibration.

It is believed that the many advantages of this invention will now be apparent to those skilled in the art. It will also be apparent that a number of variations and modifications may be made in this invention without departing from its spirit and scope. Accordingly, the foregoing description is to be construed as illustrative only, rather than limiting. This invention is limited only by the scope of the following claims.

We claim:

1. In a thermal conductivity detector of the type including a cell having sample and reference chambers enclosing respective thermal sensing and reference elements having electrical leads and wherein the cell is enclosed within a housing containing a substantially inert gaseous medium, the improvement which comprises:
    said cell being formed of a material of substantially high thermal conductivity with the sample and reference chambers each having a first and a second end and being symmetrically disposed therein;
    each of said sensing and reference elements being positioned at a first end of its respective sample or reference chamber;
    a sample gas flow passage extending through said cell and the second end of said sample chamber from a sample inlet to a sample vent;
    a reference gas flow passage extending through said cell and the second end of said reference chamber from a reference inlet to a reference vent;
    first and second thermally conductive porous members positioned and thermally clamped, respectively, at the second end of each of said sample and reference chambers and in each of the respective sample and reference gas flow passages to substantially prevent gas flow cooling of the sensing and reference elements; and
    thermally conductive means extending between said cell and said housing to control the thermal time constant of the cell.

2. The improvement of claim 1 wherein:
    the cell defines respective openings through which pass electrical leads from the sensing and reference elements in said chambers; and
    the respective first ends of said chambers being filled with thermally conductive resin for sealing such leads within said openings and completing the thermal enclosure of said sensing elements.

3. The improvement of claim 1 wherein the material of said cell is copper.

4. The improvement of claim 1 wherein said thermally conductive porous members are sintered metal.

5. The improvement of claim 4 wherein said sintered metal is silver.

6. The improvement of claim 1 wherein said thermally conductive means are wires.

7. The improvement of claim 6 wherein said wires are copper.

8. The improvement of claim 1 wherein said cell is the detector for a gas chromatograph having a carrier gas supply source, said sample inlet being connected to receive the effluent carrier and sample from said chromatograph and said reference inlet being connected to receive carrier gas from said carrier gas supply.

9. The improvement of claim 8 wherein the gaseous medium within said housing comprises carrier gas.

10. The improvement of claim 1 wherein the sensing and reference elements are thermistors.

* * * * *